(12) United States Patent
Naka et al.

(10) Patent No.: US 7,327,444 B2
(45) Date of Patent: Feb. 5, 2008

(54) SUBSTRATE INSPECTION APPARATUS AND METHOD

(75) Inventors: Nobuyuki Naka, Kyoto (JP); Akihiro Katanishi, Kyoto (JP); Masaaki Magari, Kyoto (JP); Yoshiyuki Nakajima, Kyoto (JP); Kimihiko Arimoto, Kyoto (JP)

(73) Assignee: Horiba, Ltd., Kyoto (JP)

( * ) Notice: Subject to any disclaimer, the term of this patent is extended or adjusted under 35 U.S.C. 154(b) by 81 days.

(21) Appl. No.: 11/196,947

(22) Filed: Aug. 4, 2005

(65) Prior Publication Data

US 2006/0038980 A1 Feb. 23, 2006

(30) Foreign Application Priority Data

Aug. 4, 2004 (JP) ............................. 2004-228644

(51) Int. Cl.
- *G01B 11/06* (2006.01)
- *G01N 21/21* (2006.01)
- *G01N 21/65* (2006.01)

(52) U.S. Cl. .................. 356/73; 356/301; 356/369; 356/32; 356/630

(58) Field of Classification Search .................. 356/73, 356/301, 369
See application file for complete search history.

(56) References Cited

U.S. PATENT DOCUMENTS

| 6,069,690 | A | * | 5/2000 | Xu et al. ..................... 356/73 |
| 6,657,708 | B1 | | 12/2003 | Drevillon et al. |
| 2003/0081205 | A1 | | 5/2003 | Klose |

FOREIGN PATENT DOCUMENTS

| JP | 7306135 A | 11/1995 |
| JP | 11295159 A | 10/1999 |
| WO | 91/11695 | 8/1991 |
| WO | WO 96/10737 | * 4/1996 |

* cited by examiner

*Primary Examiner*—F. L. Evans

(57) ABSTRACT

The present invention provides a method and substrate examining device that sequentially and automatically measures at least the thickness and the internal stress of the thin film at a predetermined measurement point on the surface of every manufactured semiconductor substrate to perform quality control on each substrate, and reliably recognizes the cause of defects to improve productivity. The examining device and method accurately analyzes the correlation between film thickness and stress to establish the manufacturing processes necessary for manufacturing a semiconductor substrate of higher performance, and measures the distribution of a physical quantity such as internal stress, index of refraction, and composition of the semiconductor substrate in the film thickness direction, without being influenced by change in ambient environmental temperature thereby further improving examination precision.

22 Claims, 12 Drawing Sheets

Fig. 10

| Unit | Maker | Composition unit | Model | Specification |
|---|---|---|---|---|
| Raman | HORIBA Jobin Yvon | | LabRAM series | 300 (Focal lenth of spectrgraph : 300mm) |
| | | | | HR-800(Focal length of spectrograph : 800mm) |
| | | | | ARAMIS (Automation system) |
| | | | | IR (with FT-IR) |
| | | | U-1000 | Double monochromator |
| | | | T64000 | Triple monochromator |
| Typical laser of excitation line for Raman | Coherent (USA) | Laser head | INNOVA I-Line | Water cooled Ar laser, 363.8nm, 50mW |
| | | Power supply | | 208V, 60A |
| | | Heat Exchanger | | - |
| | KIMMON Electric Co., Ltd. (Japan) | Laser head | IK3201R-F | He-Cd laser, 325.0nm, 20mW |
| | | Power supply | KR1801C | 100V, 10A |
| | Melles Griot (USA) | Laser head | 543-AP-A01 | Air cooled Ar laser, Tunable |
| | | Power supply | 175B-200B | 200V, 30A |
| | | Remote fan | 6029 | - |
| | | Remote controller | IRC-003 | - |
| | JDS Uniphase (USA) | Laser head | 2218-030SLS | Air cooled Ar laser, 488nm, 30mW |
| | | Power supply | 2110U-SLS | 100V, 20A |
| | | Remote fan | 152CFM 115V STANDARD | - |
| | | Remote controller | Remote interface controller | |
| Ellipsometer | HORIBA Jobin Yvon | - | PZ2000-LE | Laser ellipsometer |
| | | | UVISEL | Spectroscopic ellipsometer |
| | | | MM-16 | Spectroscopic ellipsometer |
| X-Y stage | Nano Control Co., Ltd. (Japan) | X-Y stage | - | Stepping motor and piezo drive |
| | | Controller | - | Special design for 12 inch wafer |
| Wafer table | - | Ceramics table and unit | Special model(for only HOR) | 6, 8, 12 inch wafer |
| | | Aluminum table and unit | Special model(for only HOR) | 6, 8, 12 inch wafer |
| Vibration isolator | Tokkyokiki Corporation (Japan) | Rigid base plate. | alpha 4G-201M-1814-HS1 | Air spring / Active isolation |
| | | Active isolation unit | | |
| | Isolation table | Isolation frame | | |
| Wafer transport equipment | HIRATA Corporation (Japan) | Robot | AR-WL180CL4-T-300-M | 8, 12 inch wafer (Double arm) |
| | | Aligner | KWA-12 | 8, 12 inch wafer |
| | | Foup opener | KWF-12B-8M | 12inch Foup and 8inch Open cassette |
| | | Body | | - |

Fig. 11

| Unit | Maker | Composition unit | Model | Specification |
|---|---|---|---|---|
| Pattern Recognition system | SONY | CCD camera | XC-ES30 | 1/3 type IT CCD, EIA |
| | COGNEX | Video Capture Board | VPM-8100X-0000 | - |
| Other units and parts | HORIBA | Fame<br>PC<br>FFU<br>Power supply<br>etc. | - | - |

SUBSTRATE INSPECTION APPARATUS AND METHOD

BACKGROUND OF THE INVENTION

1. Field of the Invention

The present invention relates to an apparatus and method for inspecting substrates such as semiconductor wafers and liquid crystal panels, more specifically to a substrate inspection apparatus for automatically measuring stress and/or a composition of thin films provided on a surface of a substrate or various patterned microfabricated parts, and further, can provide thickness and the index of refraction of the thin film at the time of measurement.

2. Description of the Prior Art

In a semiconductor manufacturing process, quality control of a substrate such as a semiconductor wafer is extremely important. Particularly, acquiring physical information such as thickness, index of refraction, stress and composition of the thin film prepared on the surface of the semiconductor wafer and the like and controlling the same so as to be in an appropriate state, is necessary to maintain a stable performance of the semiconductor device and the electronic circuit fabricated on the semiconductor wafer.

A CMOS circuit is used to achieve a high performance large-scale integrated circuit (LSI) in a sub-100 nm region in the semiconductor device, and high performance, high-speed of CMOS circuit are essential factors in manufacturing semiconductors. In order to have the CMOS circuit of high performance and high-speed, a method of shortening the gate length and a method of increasing the carrier speed are proposed, but if the circuit is miniaturized to shorten the gate length, a short channel effect occurs and thus miniaturization of the circuit has limitations.

Recently, for a technique of achieving high-performance without greatly shortening the gate length, a technique of manufacturing semiconductor devices using strained silicon with carrier mobility far greater than the normal silicon has been considered. This is a technique of improving carrier mobility by forming a silicon layer on a SiGe layer, where the lattice constant is larger than that of silicon, and applying tensile strain on the silicon layer (thin film) to modulate the silicon band structure. Further, in order to improve the performance of the MOSFET while suppressing the short channel effect, thin filming of the gate oxide film is performed but the procedure has limitations, and thus the strained silicon technique is again given attention as a means for providing a MOSFET of high performance without involving thin filming of the oxide film.

In recent semiconductor wafer manufacturing, it is necessary to perform an examination associated with thickness and stress measurement of the thin film to improve quality control/productivity. A Raman spectroscopic technique is conventionally known for a stress measurement of semiconductor materials such as silicon. The stress measurement using the Raman spectroscopic technique is such in which the stress at the measurement point is estimated from a change of peak positions of the Raman spectrum by using the fact that the Raman spectrum shifts when stress acts on the single crystal silicon and the like.

In Japanese Laid-Open Patent Publication No. 8-5471, the structure of a stress measurement method and a stress measurement device for performing stress measurement using Raman spectroscopy in a semiconductor device manufacturing process is disclosed. Inspection of each part relating to stress in the manufacturing process is performed by means of the stress measurement device disclosed in Japanese Laid-Open Patent Publication No. 8-5471 so as to improve quality control and productivity.

However, since the stress measurement apparatus disclosed in Japanese Laid-Open Patent Publication No. 8-5471 cannot sequentially and automatically measure the surface of a plurality of wafers, the quality evaluation cannot be sufficiently performed on all the manufactured semiconductor wafers or the semiconductor devices, and an accurate process control in the manufacturing process of the wafer becomes difficult. Further, in obtaining film thickness in addition to stress for each microfabricated part, it is important to find a correlation between stress and film thickness in manufacturing the semiconductor wafer, but stress and film thickness cannot be measured for the wafer.

In addition, it is supposed that when embedding a thick oxide film such as a trench configuration in the semiconductor device, a particularly significant stress concentration is likely to occur near the microfabricated part. Thus, if the thick oxide film is formed at the microfabricated part in the sub-100 nm region, stress produced at the interface of the thin films becomes great and heat or stress is generated even when stress similar to when forming a relatively thin oxide film is acted, which may become the cause of defects such as thermal migration or stress migration. Therefore, finding the relationship between stress and film thickness at the same microscopic region becomes important in quality control of the wafer.

In developing future semiconductor wafers, in particular, the strained silicon technique is likely to be introduced and thus the strained silicon tends to be formed in the semiconductor wafer. Therefore, measuring various physical quantities such as internal stress and film thickness of the strained silicon, and further, composition of SiGe layer serving as a base layer, and analyzing the correlation between film thickness and stress are becoming increasingly important, and adjusting the manufacturing process so as to control the conditions of stress and film thickness to be optimum and manufacturing the semiconductor wafer so as to manufacture an integrated circuit of higher performance are extremely important. In manufacturing the semiconductor wafer adopting the strained silicon technique, the inspection process of all the manufactured wafers is considered necessary, but a substrate inspection apparatus for simply and easily performing stress measurement and film thickness measurement does not exist.

In a laser anneal equipment disclosed in Japanese Laid-Open Patent Publication No. 9-213652, a Raman spectroscopic photometer and an ellipsometer are mounted to allow measurement of structure and index of refraction of the crystalline silicon film immediately after laser anneal, but since the measurement points of the Raman/ellipsometer optical systems differ each other, various physical information at a specific microscopic region cannot be obtained all at once. Further, an equipment of Japanese Laid-Open Patent Publication No. 9-213652 is included in the equipment of the manufacturing process and thus is difficult to be applied for use as an inspection apparatus.

SUMMARY OF THE INVENTION

The present invention provides a substrate inspection apparatus that sequentially and automatically measures at least the thickness and the internal stress of the thin film at a predetermined measurement point on the surface of each manufactured semiconductor substrate to strictly perform quality control. It can reliably recognize the cause of defects to improve productivity, and accurately analyze the correlation between film thickness and stress to establish the manufacturing processes necessary for manufacturing a semiconductor substrate of higher performance. The present invention can measure the distribution of a physical quantity or characteristic such as internal stress, index of refraction, and composition of the semiconductor substrate in the film thickness direction, and can accurately measure the physical quantity without being influenced by change in ambient environmental temperature thereby further improving inspection precision.

In order to achieve the aims mentioned above, a substrate inspection apparatus is characterized by including a sample stage configured so as to be movable, a conveying device for conveying a sample to be measured to the sample stage, an optical microscope for observing a measurement point on the sample to be measured on the sample stage, an ellipsometric optical system for irradiating a polarized light of multiple wavelengths to the measurement point and outputting information relating to the sample to be measured. A Raman spectroscopic optical system for irradiating a laser light to the measurement point of the optical microscope and outputting different information relating to the sample to be measured is provided, and an arithmetic processing unit analyzes and outputs a measurement of stress and/or composition in addition to film thickness and/or index of refraction at the measurement point using the obtained information.

A substrate inspection apparatus is further characterized by a plurality of laser light sources of different wavelength and a laser light selecting device for selectively and automatically switching the laser light for irradiating to the measurement point on the sample to be measured from the plurality of laser light sources arranged in the Raman spectroscopic optical system.

A reference sample may be arranged at a position in the vicinity of the sample to be measured on the sample stage, and the information relating to the sample output from the ellipsometric optical system and the Raman spectroscopic optical system can be desirably calibrated with the information obtained by measuring the reference sample as necessary with the ellipsometric optical system and the Raman spectroscopic optical system as a reference.

Measurements by the ellipsometric optical system and the Raman spectroscopic optical system can be performed after an initial position adjustment in the height direction of the sample stage while checking the position of the focal point thereof by using an image observed by the optical microscope or the intensity of the light obtained when the laser light is irradiated to the sample.

An arithmetic processing unit includes an inspection recipe program and data of coordinates indicating the position of the measurement point on the sample, measurement condition data containing information of the wavelength region of the light used in the Raman spectroscopic optical system and the ellipsometric optical system, the measurement time, and the calibration curve used, and the data format of inspection results. The substrate inspection apparatus may include an automatic inspection function for sequentially performing the same inspection on a plurality of samples in accordance with the inspection program or routine in an automatic manner.

The arithmetic processing unit further can include a stored recognition image formed by an image observed by the optical microscope at the measurement point on the sample as the data indicating the position of the measurement point of the inspection recipe data, and measurements, using the ellipsometric optical system and the Raman spectroscopic optical system, is performed after moving the sample stage in the direction of the plane surface and adjusting the plane surface position of the measurement point by comparing the image obtained by observing the surface of the sample with the optical microscope and the recognition image.

Further, a substrate inspection apparatus is characterized by including a sample stage configured so as to be movable, a conveying device for conveying a sample to the sample stage, an optical microscope for observing a measurement point on the sample on the sample stage, a Raman spectroscopy optical system for irradiating a laser light to the measurement point of the optical microscope and outputting information relating to the sample to be measured, and an arithmetic processing unit for analyzing and outputting stress or strain at the measurement point using the obtained information, where a plurality of laser light sources of different wavelength and a laser light selecting device capable of selectively and automatically switching the laser light for irradiating to the measurement point on the sample to be measured from the plurality of laser light sources are arranged in the Raman spectroscopic optical system.

A reference sample is arranged at a position in the vicinity of the sample of the sample stage, and the information relating to the sample output from the Raman spectroscopic optical system can be desirably calibrated with the information obtained by measuring the reference sample by means of the Raman spectroscopy optical system as a reference.

A thickness of the thin film, is measured at high precision using the ellipsometric optical system at a microscopic region of the surface of the sample, and the stress is also measured with good precision using the Raman spectroscopic optical system at the same microscopic region. That is, by measuring both film thickness and stress of the thin film at the same microscopic region with high precision and simultaneously outputting or displaying the same, the film thickness dependency on stress is found. The manufacturing processes may be appropriately adjusted to manufacture a semiconductor substrate that does not create concentration of stress with a thin film of a desired film thickness formed. Further, since the measurement point can be observed by including the optical microscope, the operator is able to check the state of the surface of the sample to be measured through observation and thus the operation is further facilitated.

In particular, the Raman spectroscopic optical system is suitable for measuring stress applied to a microscopic region or composition at high precision, and the ellipsometric optical system is suited for measuring film thickness and index of refraction at the microscopic region at high precision. Therefore, for a semiconductor substrate, the combination of the Raman spectroscopy optical system and the ellipsometer optical system is most suitable for measuring stress and film thickness, which are important physical quantities in manufacturing the semiconductor substrate with its performance or durability being optimum. Particularly, since a strained silicon technique has been recently adopted in manufacturing the semiconductor substrates, the fact that the Raman spectroscopic optical system and the ellipsometric optical system measures the correlation between stress and film thickness at the same microscopic region significantly contributes to an advancement of productivity and technique in such field.

Further, since all manufactured semiconductor substrates are taken out one by one to sequentially obtain the measurement value of stress or film thickness at a surface thereof, examinations of each semiconductor substrate becomes possible, and reliability of a semiconductor substrate manufactured by performing an extremely precise product management is enhanced. Further, as the cause is more easily investigated from the measurement result when defects occur, the productivity may be also enhanced.

In addition to the advantage of being able to simultaneously obtain the information of stress and film thickness which are physical quantities essential in manufacturing the semiconductor substrate with its performance or durability being optimum with a combination of the Raman spectroscopic optical system and the ellipsometric optical system and measure the correlation at the same microscopic region, when measuring stress or composition by means of the Raman spectroscopy optical system, the distribution in the depth direction (film thickness direction) of stress or composition of the sample to be measured is easily measured by selectively and automatically switching and irradiating the laser light of different wavelength to the measurement point on the sample from a plurality of laser light sources. Thus even when having a semiconductor substrate using strained silicon as the object to be measured, various physical quantities such as internal stress of the strained silicon and composition of the SiGe layer serving as a base layer are reliably measured and substrate inspection is performed at a higher precision in an automatic manner.

A reference sample can be arranged at a position in the vicinity of the sample to be measured adjacent the sample stage, and when calibrating the information relating to the sample output from the ellipsometric optical system and the Raman spectroscopic optical system with the information obtained by measuring the calibration sample as necessary with the ellipsometer optical system and the Raman spectroscopy optical system as the reference) even when wavelength shift occurs from the strain of optical components and the like or shift of peak shift of the Raman spectrum occurs due to variation of optical system such as deterioration of the optical filter or temperature influence of the sample itself to be measured originating from the fluctuation of ambient environmental temperature. Calibration is performed based on the information obtained through measurement of the calibration sample, and various physical quantities are accurately measured and the precision of substrate inspection is further enhanced irrespective of the fluctuation of the environmental temperature.

Further, when performing measurement using the ellipsometer optical system and the Raman spectroscopy optical system after performing position adjustment in the height direction of the sample stage while checking the position of the focal point thereof by using an image observed by the optical microscope or the intensity of the light obtained when the laser light is irradiated to the sample to be measured, the ellipsometer optical system and the Raman spectroscopy optical system reliably focuses the focal points at the measurement point by a position adjustment in the height direction of the sample stage even when warp is created at the sample, and thus film thickness or index of refraction is analyzed at the measurement point with high precision.

The arithmetic processing unit includes inspection recipe data comprising coordinates indicating the position of the measurement point on the sample to be measured, the measurement condition containing information of wavelength region used in the Raman spectroscopic optical system and the ellipsometer optical system, the measurement time, a point, and the calibration curve used, and inspection result output condition indicating the output format and parameters of the inspection result. The substrate inspection apparatus may include an automatic examination function for sequentially performing the same examination on a plurality of samples to be measured in accordance with the examination recipe data, a common inspection according to the measurement conditions set using the inspection recipe data is sequentially and automatically performed on all the samples to be measured. Further, the measurement conditions are easily changed by changing the inspection recipe data.

When the arithmetic processing unit includes a recognition image formed by an image observed by the optical microscope at the measurement point on the sample as the data indicating the position of the measurement point of the inspection recipe data, and when performing the measurement using the ellipsometric optical system and the Raman spectroscopic optical system after moving the sample stage in the direction of the plane surface and adjusting the plane surface position of the measurement point by comparing the image obtained by observing the surface of the sample with the optical microscope and the recognition image. The physical information of the measurement point corresponding to the part of a specific circuit pattern is automatically inspected with an electronic circuit already formed on the sample to be measured. That is, the determination of whether the measurement point corresponding to the part of a specific circuit pattern is in a state of exhibiting a sufficient performance or not is made in advance from the measurement values of film thickness or stress at the measurement point.

The stress at the microscopic region and the like is measured in high precision using the Raman spectroscopic optical system at the microscopic region of the surface of the sample. That is, the manufacturing process thereof is appropriately adjusted to manufacture a semiconductor substrate forming a thin film applied with stress of an appropriate strength. Further, as the measurement point is observed by including the optical microscope, the operator is able to check the state of the surface of the object through observation, and thus the operation is facilitated.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 10 is an equipment table for the first embodiment;

FIG. 11 is a supplemental equipment table for the second embodiment.

DETAILED DESCRIPTION OF THE PREFERRED EMBODIMENTS

Reference will now be made in detail to the preferred embodiments of the invention which set forth the best modes contemplated to carry out the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to unnecessarily obscure aspects of the present invention.

Figure 1A:
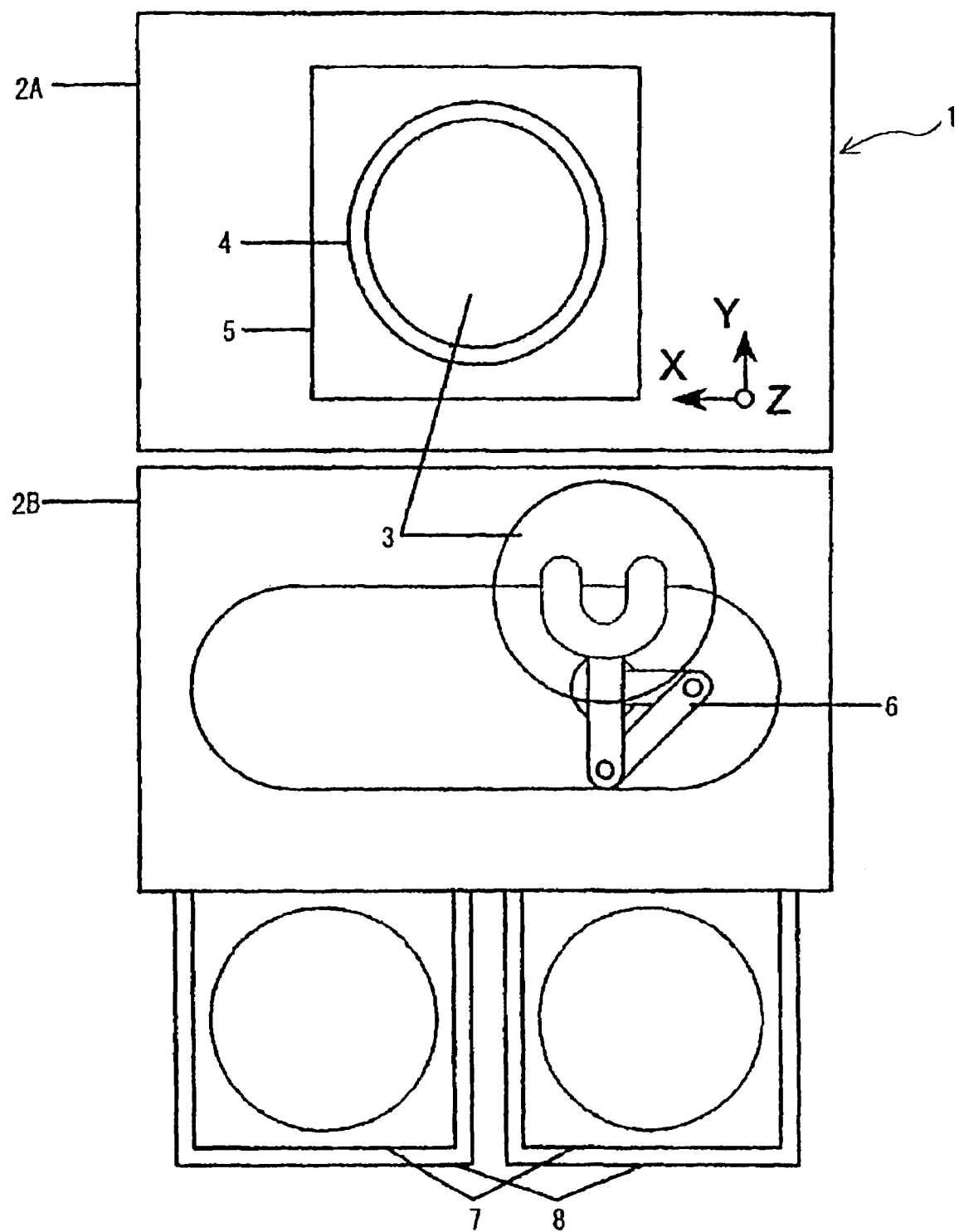
FIG. 1A is a plan view schematically showing an entire configuration of a substrate inspection apparatus according to a first embodiment of the present invention.
Figure 2:
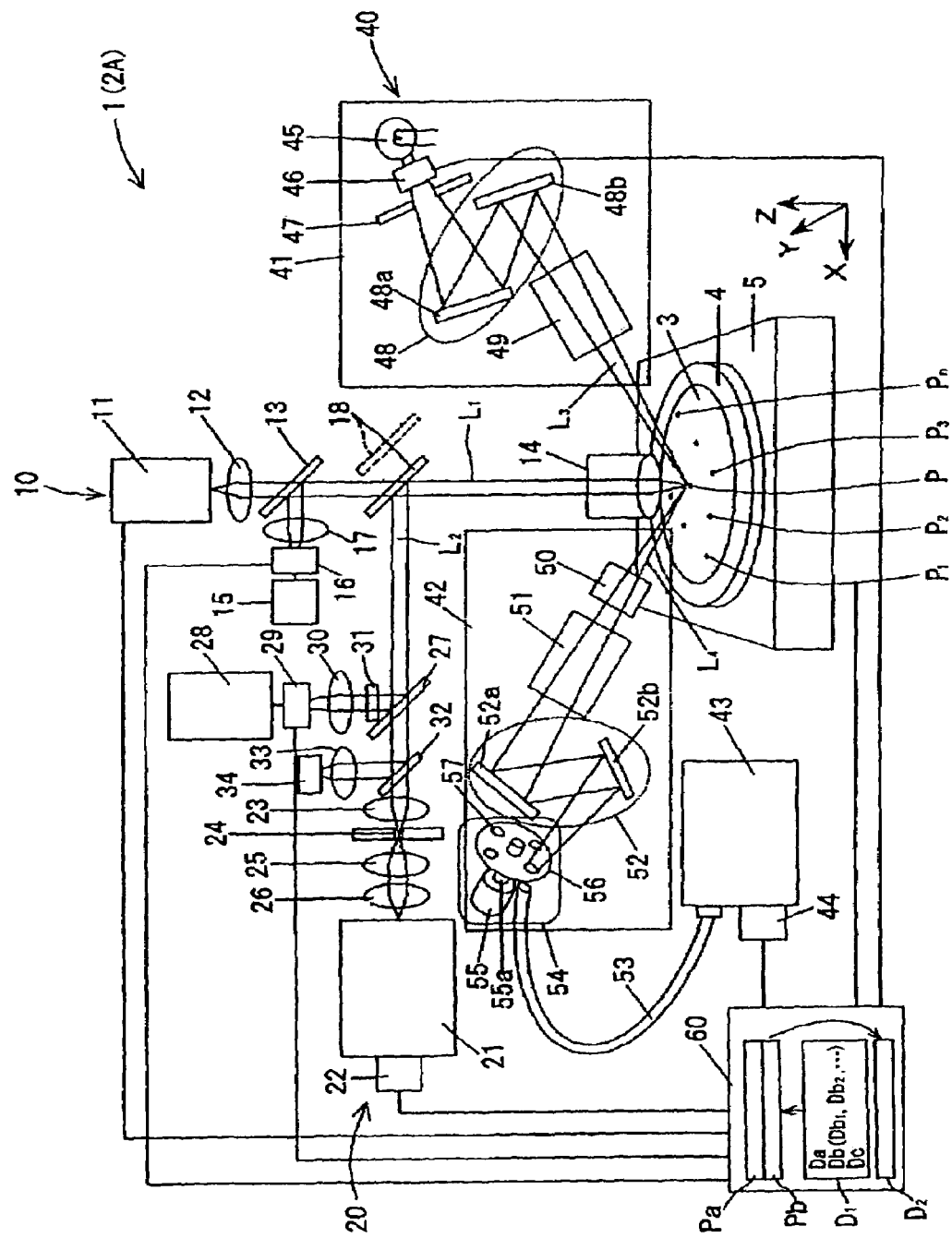
FIG. 2 is a view showing a configuration of a main part of the substrate inspection apparatus according to the first embodiment.

FIG. 1A is a plan view schematically showing an entire configuration of a substrate inspection apparatus 1 according to a first embodiment of the present invention and FIG. 2 is a view showing a configuration of a main part of the substrate inspection apparatus 1. In FIG. 1A, 2A is a measuring chamber of the substrate inspection apparatus 1 equipped with a Raman spectroscopic optical system/ellipsometric optical system, 2B is a transport equipment set up next to the measuring chamber 2A, 3 is a substrate (sample, hereinafter referred to as a wafer) of for example, a silicon wafer formed by applying the strained silicon technique where the thin film of silicon layer is formed on the SiGe layer with large lattice constant, 4 is a sample stage configured so as to be movable in a three-dimensional direction of horizontal direction (X, Y directions) and height direction (Z direction), and 5 is a driving section of the sample stage 4.

Figure 6:
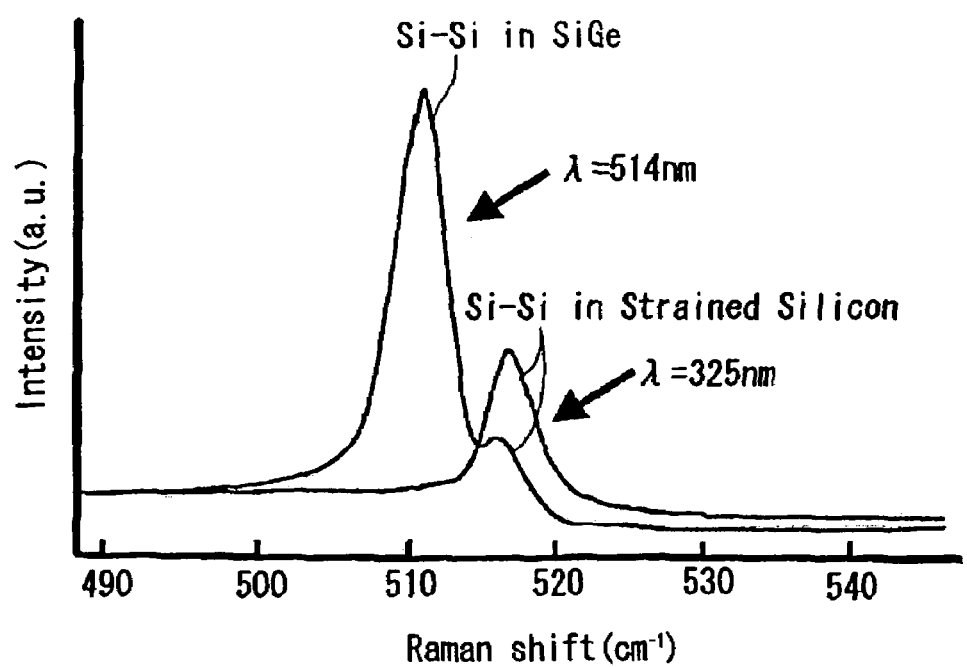
FIG. 6 is a view showing a relationship of wavelength and spectral intensity in Raman spectrum measurement of the strained silicon substrate.

In FIG. 1A, 6 is a robot arm with a function of grasping the wafer 3 and transporting the same onto the sample stage 4, 7 is a case for accommodating a plurality of wafers 3 so as to be stacked in a longitudinal direction with a predetermined spacing, and 8 is a case table or stand for mounting the case 7. The wafer 3 accommodated so as to be stacked in the longitudinal direction, for example, is taken out one by one and transported to the sample stage 4 and the examined wafer 3 is again returned to the original location by means of the robot arm 6. However, when arranging two cases 7 next to each other as in the first embodiment, the wafer 3 taken out from one case 7 and examined may be accommodated in the other case 7 one by one.

Figure 1B:
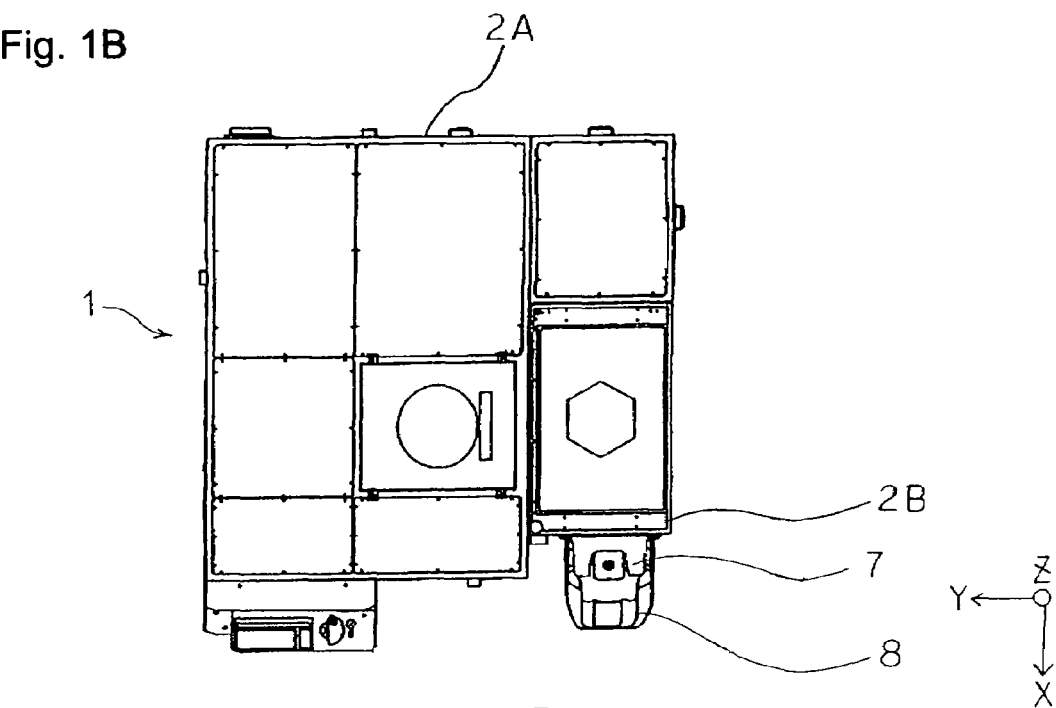
FIG. 1B is a plan view of a substrate inspection apparatus.
Figure 1C:
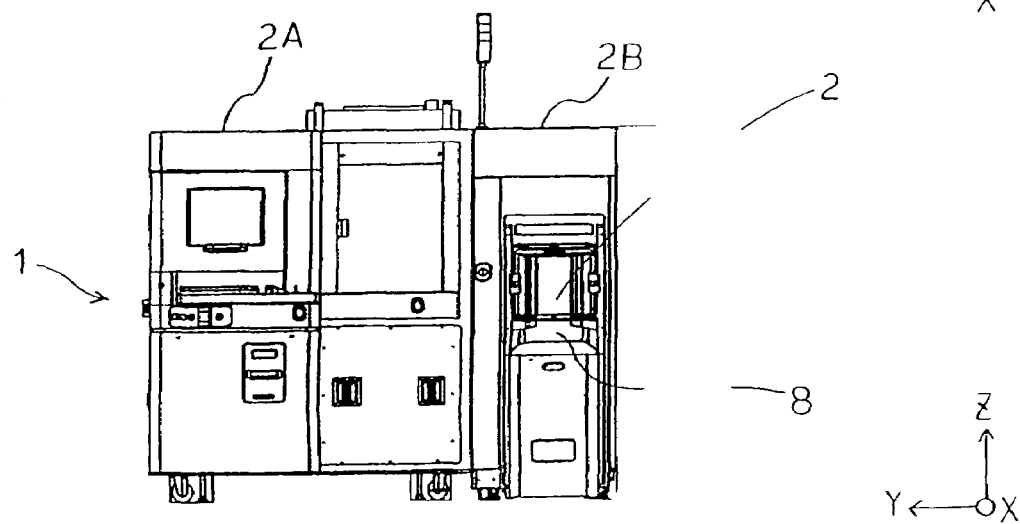
FIG. 1C is a front elevational view.
Figure 1D:
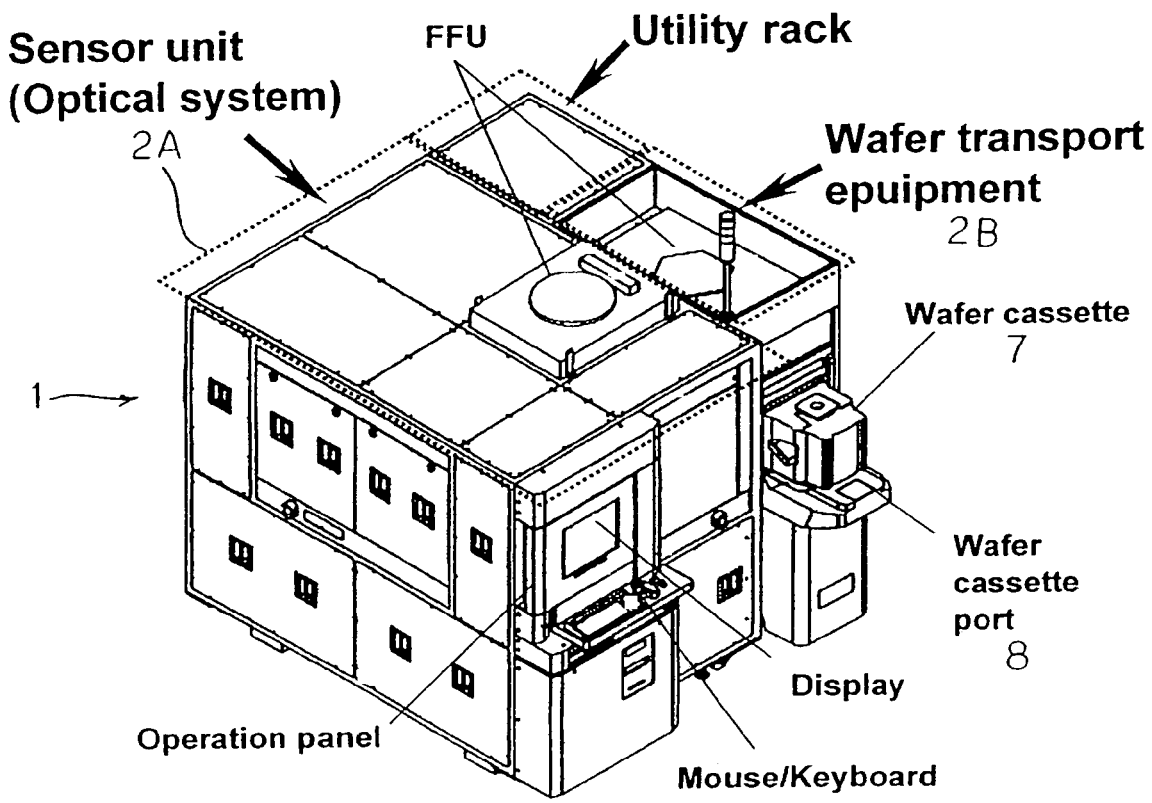
FIG. 1D is a front perspective view.
Figure 1E:
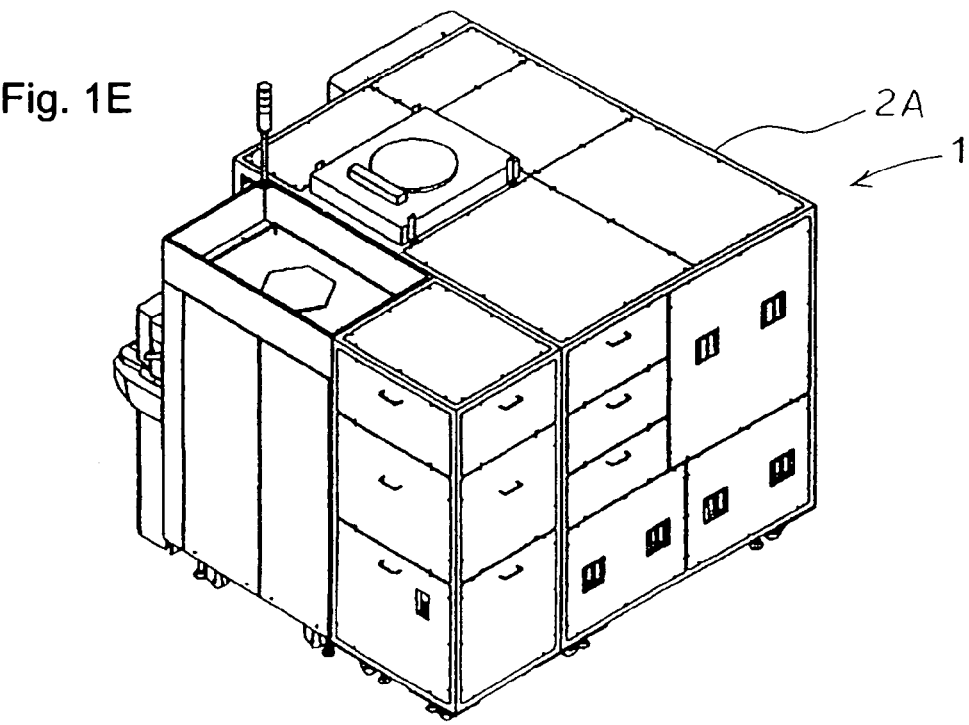
FIG. 1E is a rear perspective view.

FIG. 1B is a plan view while FIG. 1C is a front elevational view. FIG. 1D is a front perspective view while FIG. 1E is a rear perspective view.

The wafer substrate 3, sample stage 4 and stage drive 5 are installed inside the measurement chamber 2A. The robot arm 6 is installed inside the carrying apparatus 2B.

In FIG. 2, 10 is an optical microscope for observing the surface of the wafer 3. The optical microscope 10 including a CCD camera 11 arranged on an optical axis $L_1$ at substantially right angles to the surface of the wafer 3, a collective lens 12 arranged on the optical axis L1, a beam splitter (half mirror) 13, an objective lens 14, a white light source 15 for irradiating a white light to the wafer 3 by way of the half mirror 13, a shutter 16 and a collimator lens 17. Further, 18 is a movable mirror arranged on the optical axis $L_1$, and a measurement point P of a microscopic region at the surface of the wafer 3 is observed with the optical microscope 10 by moving the mirror 18 to a position shown with a virtual line in FIG. 2. It is to be noted that the white light source 15, the shutter 16, and the collimator lens 17 are arranged on an optical axis perpendicular to the optical axis $L_1$.

20 is a Raman spectroscopy optical system for irradiating the laser light onto the wafer 3 and detecting the Raman light using the optical axis $L_1$ same as the optical microscope 10 by moving the mirror 18 to a position shown with a solid line in FIG. 2. The Raman spectroscopy optical system 20 includes a spectroscope 21 arranged on the optical axis $L_2$ reflected by the mirror 18 so as to be in a direction perpendicular to the optical axis $L_1$, a detector 22 for detecting the spectral Raman light, a lens 23 for adjusting the Raman light entering the spectroscope 21, a pin hole 24, a collimator lens 25, a collective lens 26, (5) a notch filter or edge filter 27 for reflecting only the Rayleigh light of the Raman analysis, a laser light source 28 for irradiating the laser light using (5) the notch filter or edge filter 27, a shutter 29, a collective lens 30, an optical filter 31 for removing the light of wavelength other than the laser light that excites the Raman light, a beam splitter 32 for reflecting 5 to 10 percent of the light at the back of the notch filer 27 on the optical axis $L_2$, a collective lens 33 and a detector 34 for focal point detection.

It is to be noted that the Raman spectroscopy optical system 20 is configured so as to use the objective lens 14 in common with the optical microscope 10. Further, the laser light source 28, the shutter 29, the collective lens 30, and the optical filter 31 are arranged on an optical axis perpendicular to the optical axis $L_2$. Similarly, the beam splitter 32, the collective lens 33 and the detector 34 are arranged on a different optical axis perpendicular to the optical axis $L_2$.

40 is an ellipsometer optical system arranged to irradiate a polarized light $L_3$ of multiple wavelengths to the measurement point P on the wafer 3 to where the optical microscope 10 is focused and to output physical information at such measurement point. The ellipsometer optical system 40 includes an incidence optical system 41 for irradiating the polarized light $L_3$ to the surface of the wafer 3 on the sample stage 4 diagonally from above on one side, a detection optical system 42 arranged diagonally above with respect to the surface on the other side of the sample stage 4, a spectroscope 43 and a detector 44.

The incidence optical system 41 is configured from a white light source 45 made of for example, xenon lamp that emits a light of wide wavelength region of for example, 190 to 830 nm, a shutter 46, a slit 47 for narrowing the light emitted from the white light source 45, a beam reducing optical system 48, and a polarizer 49. The beam reducing optical system 48 includes for example, two concave mirrors 48a, 48b.

The detection optical system 42 is arranged to output variation of polarization $L_4$ reflected when the polarized light $L_3$ is irradiated onto the measurement point P of the surface of the wafer 3 to, for example, the spectroscope 43, and includes a phase modulated element 50, an analyzer 51, a beam reducing optical system 52 consisting of two concave mirrors 52a, 52b, and an optical fiber 53 for retrieving a signal for the spectroscope 43, where a pin hole section 54 is arranged between the beam reducing optical system 52 and the optical fiber 53.

The pin hole section 54 is formed by opening a plurality of pin holes 57 of a size (diameter) different from each other at an appropriate spacing on the same circumference of a circular plate 56 attached to a rotating shaft 55a of for example, a stepping motor 55. Therefore, as shown in FIG. 2, the light exiting from the beam reducing optical system 52 enters the optical fiber 53 through the pin hole 57 only when one of the pin holes 57 is positioned on a light path connecting the beam reducing optical system 52 and the optical fiber 53.

60 is an arithmetic processing unit (hereinafter referred to as a computer) connected to the driving section (not shown) of the movable mirror 18 and the like in addition to the conveying device 2B, the driving section 5 of the sample stage 4, the optical microscope 10, the Raman spectroscopy optical system 20, and the ellipsometer optical system 40 to control the entire substrate inspection apparatus 1. A control program Pa indicating the operation of an examination sequence of sequentially taking out the wafer 3 one by one from a plurality of wafers 3 accommodated in the case 7, arranging one of the wafer on the sample stage 4, executing a series of examinations on each wafer 3 in such state and accommodating the examined wafer 3 again in the case 7 by controlling for example, the conveying device 2B, the driving section 5 of the sample stage 4, the optical microscope 10, the Raman spectroscopy optical system 20, and the ellipsometer optical system 40. An examination result output program Pb provides an indication of the operation of performing an arithmetic process on the examination results and displaying a result on a screen (not shown) or recording the result in a medium including an examination recipe data $D_1$ formed by recording the measurement condition, and an examination result output condition and the like for each wafer 3 is stored as data $D_2$ of the examination result and recorded in the computer 60.

The examination recipe data $D_1$ includes measurement point data Da, measurement condition data Db, and output condition data Dc. The measurement point data Da is obtained by setting for example, a few to more than a dozen points of measurement points $P_1$ to $P_n$ (include measurement point P in the state shown in FIG. 2) at an equidistant on the surface of each wafer 3, and recording the coordinates indicating the position of each measurement point P, $P_1$ to $P_n$, where n measurement points $P_1$ to $P_n$ are set at equidistant in a two-dimensional direction in the example shown in FIG. 2.

The measurement condition data Db is the data containing information indicating the wavelength region Db1 of the light used in for example, the optical microscope 10, the Raman spectroscopy optical system 20, and the ellipsometer optical system 40. The accumulated time Db2 indicates the accumulated time of detecting the light with each detector 22, 44, and various analytical curves Db3 are used when obtaining stress or composition of the thin film and film thickness or index of refraction of the thin film from the intensity of light of each wavelength or the shifted amount of the spectrum detected by each detector 22, 44.

Further, the output condition data Dc shows the output pattern $Dc_1$ for setting the output layout by selecting stress, film thickness and the like as the physical quantity to be output among the physical quantity obtained as the examination result and the like, and specifying the way of representing the correlation between stress and film thickness. The output pattern $Dc_1$ includes for example, a setting of defining the upper limit and the lower limit of each physical quantity and outputting those exceeding the limit range as defects, and a setting of outputting statistics such as variation of each physical quantity for every plurality of measurement points $P_1$ to $P_n$ or for each wafer.

Further, the correlation between stress and film thickness may be represented with a function for deriving an estimated value of carrier mobility from the measurement values of for example, stress and film thickness. It is to be noted that the function expressing the correlation may be derived based on the carrier mobility calculated by actually measuring the stress and the film thickness using a plurality of the wafer 3 as sample in advance, and actually measuring the properties of CMOS circuit after forming the CMOS circuit. Further, since the function is information contained in the output condition data Dc, it may be updated as needed in accordance with the actual measurement value.

Therefore, the control program Pa executes an examination complying with the same criteria for each wafer 3 with reference to the measurement point data Da and the measurement condition data Db contained in the examination recipe data $D_1$. The examination result output program Pb displays the measurement value of each physical quantity obtained through examination of each measurement point $P_1$ to $P_n$ on the surface of each wafer 3 using the screen (not shown) and the like in the output layout defined in advance as the output pattern $Dc_1$ of the examination result output condition data Dc with reference to the output condition data Dc contained in the examination recipe data $D_1$ or records the same as stored data $D_2$ of the examination result.

By the way, the content of an inspection recipe is shown as follows:

1. Setting of measurement conditions of Raman spectrophotometric system
   (1) Excitation wavelength (laser wavelength)
   (2) Diffraction grating
   (3) Center of measurement range
   (4) ND filter (adjustment of laser power)
   (5) Hole diameter (confocal optical system)
   (6) Entrance slit width (spectroscope)
   (7) Measurement data integrated time
   (8) Number of accumulated spectra
   (9) Setting of presence or absence of auto-focus
   (10) Range of curve fitting (plurality acceptable)
   (11) Fitting curve function (Gauss/Lorentz/Gauss+Lorentz)
   (12) Number of fitting curves
   (13) Initial value of fitting curve
      [1] Peak shift, peak intensity, half-value width
   (14) Arithmetic expression
      Ex. Stress-strain value calculation calibration curve
   (15) Output parameters
      Peak shift, peak intensity, half-value width, stress, strain, etc.
2. Setting of measurement point coordinates 3. Setting of measurement conditions of calibration samples Content is same as that of the above (1) through (15) for each sample.
4. Setting of presence or absence of measurement of calibration samples The operation of each part from the operation of the control program Pa will now be explained. When the worker places the case 7 accommodating a plurality of wafers 3 on the case table 8 and operates the substrate examination device 1, as shown in FIG. 1, the robot arm 6 of the conveying device 2B takes out one wafer 3 from the case 7 and arranges the wafer on the sample stage 4 under control of the computer 60.

Next, the position of the wafer 3 is moved in the Z direction (height direction) and the X-Y direction (horizontal direction) so that the focal point of the optical microscope 10 coincides with one of the measurement point P of a plurality of measurement points $P_1$ to $P_n$ indicated in the measurement point data Da by controlling the driving section 5 by means of the computer 60 while maintaining the wafer 3 at a horizontal state. Further, since the measurement point P shifts in the height direction due to the warp of the wafer 3, the final positioning is performed by moving the driving section 5 in the Z direction while observing the image of the surface of the wafer 3 by means of the optical microscope 10 or the Raman spectroscopy optical system 20.

That is, when performing positioning in the Z direction using the optical microscope 10, the computer 60 only opens the shutter 16 of the optical microscope 10 with the shutters 29, 46 of the Raman spectroscopy optical system 20 and the ellipsometer optical system 40 closed and the reflective mirror 18 moved to the position shown with the virtual line, so that the light from the white light source 15 is reflected by the half mirror 13 and is irradiated onto the surface of the wafer 3 through the objective lens 14. The light from the surface of the wafer 3 transmits through the objective lens 14 and the half mirror 13 and enters the CCD camera 11 by means of the collective lens 12, and thus the computer 60 obtains the image at the focal position of the objective lens 14. When the focal point of the image obtained by the optical microscope 10 is shifted, the computer 60 exercises control so as to appropriately move the driving section 5 in the Z direction (vertical direction) and align the focal positions.

The optical axis and the focal point of the ellipsometer optical system 40 are adjusted in advance so as to be the same as the focal point of the optical microscope 10 at the surface of the wafer 3. Therefore, when the focal point of the optical microscope 10 is fine adjusted by the alignment operation, the ellipsometer optical system 40 irradiates the polarized light $L_3$ to the measurement point P same as the optical microscope 10 to obtain the physical information at the measurement point P.

When the image (pattern) recognizable by the optical microscope 10 is not obtained at the surface of the wafer 3, the computer 60 only opens the shutter 29 of the Raman spectroscopy optical system 20 with the shutters 16, 46 of the optical microscope 10 and the ellipsometer optical system 40 closed and the reflective mirror 18 arranged at a position shown with the solid line, so that the laser light from the laser light source 28 is reflected by the reflective mirror 18 and is irradiated onto the surface of the wafer 3 through the objective lens 14. The Raman light from the surface of the wafer 3 is thereby reflected by the objective lens 14, the reflective mirror 18, and the beam splitter 32, and enters the detector 34 and thus the computer 60 defines the focal position of the objective lens 14 using the intensity of the light obtained when the laser light is irradiated on the surface of the wafer 3.

When the wavelengths of the light measured by the Raman spectroscopy optical system 20 and the optical microscope 10 greatly differ, the focal points of the Raman spectroscopy optical system 20 and the optical microscope 10 are considered to be slightly shifted only in the Z direction. Since the computer 60 is capable of obtaining the shifted amount of the focal position of the Raman spectroscopy optical system 20 from the wavelength region $Db_1$ of the light defined in advance by the above mentioned measurement condition data Db to be used, the sample stage 4 is moved in the Z direction and correction of the focal position thereof is performed for measurement using the Raman spectroscopy optical system 20 and for using the optical microscope 10 and the ellipsometer optical system.

The computer 60 then measures the film thickness of the thin film of the surface of the wafer 3 using the ellipsometer optical system 40. That is, the computer 60 controls the opening of the shutter 46 of the ellipsometer optical system 40 with the shutters 16, 29 of the optical microscope 10 and the Raman spectroscopy optical system 20 closed, so that the polarized light $L_3$ from the incidence optical system 41 irradiates the surface of the wafer 3. The polarized light $L_4$ reflected by the thin film of the surface of the wafer 3 enters the spectroscope 43 by way of the detection optical system 42, and the spectral intensity of the spectral polarized light $L_5$ is detected by the detector 44. The detector 44 is set by the accumulated time $Db_2$ contained in the measurement condition data Db. The computer 60 analyzes the spectral intensity obtained from the detector 44 to obtain the film thickness of the silicon thin film at the surface of the wafer 3. It is to be noted that the physical quantity obtained using the ellipsometer optical system 40 can be film thickness but also could be the index of refraction.

Subsequently, the computer 60 measures the magnitude of stress at the thin film of the surface of the wafer 3 using the Raman spectroscopy optical system 20. The Raman spectroscopy optical system 20 is arranged on the optical axis $L_1$ same as the optical microscope 10, and thus the position in the XY direction thereof is reliably the same as the optical microscope 10. It is to be noted that when the wavelengths of the light measured with the Raman spectroscopy optical system 20 and the optical microscope 10 greatly differ, the shift of the focal points in the Z direction of the Raman spectroscopy optical system 20 and the optical microscope 10 must be corrected at this point.

The computer 60 controls the opening of the shutter 29 of the Raman spectroscopy optical system 20 with the shutters 16, 46 of the optical microscope 10 and the ellipsometer optical system 40 closed and the reflective mirror 18 moved to a position shown with the solid line, so that the laser light from the laser light source 28 is reflected at the notch filter 27 and the reflective mirror 18 and is irradiated onto the surface of the wafer 3 through the objective lens 14. The light generated at the surface of the wafer 3 is led to the optical axis $L_2$ by the objective lens 14 and the reflective mirror 18, and the Raman scattering light excluding the Rayleigh light is transmitted through the notch filter 27 and enters into the spectroscope 21 by way of various optical systems 23 to 26. The spectral intensity of the Raman scattering light spectroscoped by the spectroscope 21 is detected by the detector 22.

It is to be noted that the detector 22 is set by the accumulated time Db2 contained in the measurement condition data Db. The computer 60 analyzes the spectral intensity obtained from the detector 22 and obtains a physical quantity such as stress or composition at the measurement point P on the surface of the wafer 3 from a relationship of Raman spectrum and stress stored in advance.

As mentioned above, in the substrate inspection apparatus 1, two light sources 28, 45 for the spectroscopic analysis and one light source 15 for the optical microscope are arranged, but since shutters 16, 29, 46 are arranged at the respective light exiting part and the shutters other than the relevant shutter are closed during measurement, the light from a light source of another optical system does not adversely affect the measurement result.

Next, the physical quantity obtained using the Raman spectroscopy optical system 20 and the ellipsometer optical system 40 is output in accordance with the operation defined by the examination result output program Pb. That is, the measurement values of each physical quantity obtained by examining each measurement point $P_1$ to $P_n$ on the surface of each wafer 3 are screen displayed with the output layout set in advance as the output pattern $Dc_1$ of the examination result output condition data Dc or recorded as the stored data $D_2$ of the examination result. Further, when the upper limit and the lower limit are set for each physical quantity as the output pattern $Dc_1$, a warning alarm and the like is output to notify the worker of any abnormality if a wafer 3 exceeding such limit range is produced.

In the above mentioned example, n measurement points $P_1$ to $P_n$ dotted in a two dimensional direction are given in the measurement point data Da thereby allowing a general distribution of each physical quantity at substantially the entire surface of the wafer 3 to be found, and the time needed for examination can be shortened. However, the present invention is not limited to such an aspect, and the region to be measured may be defined in the measurement point data Da. In this case, the driving section 5 is moved at a predetermined interval to perform mapping of stress and film thickness of the surface of the wafer 3.

In the above first embodiment, an optical fiber 53 is used as a means for entering the light to the spectroscope 43 of the ellipsometer optical system 40, but it can also be applicable to the Raman spectroscopy optical system 20. On the other hand, with regards to a means of entering light into the ellipsometer spectroscope 43, the light may enter directly from a pin hole 57 to the spectroscope 43 without using the optical fiber 53.

Further, in the above first embodiment, stress is given by way of an example and explained as information obtained by analyzing the Raman spectral spectrum by means of the Raman spectroscopy optical system 20, but the present invention is not limited thereto. That is, by storing information relating to a magnitude of a physical quantity such as shifted amount of the Raman spectral spectrum, and the structure and composition or electrical property of the substrate with respect to strength in the computer 60, the Raman spectroscopy optical system 20 may be used in measuring not only stress but also other physical quantity such as structure, composition or electrical property.

Since the main hardware components of the substrate inspection apparatus of the first embodiment can be purchased from commercially available sources, a detailed explanation of their features are not necessary to a person of ordinary skill in this field. For example, a Raman unit, laser heads and power source, laser ellipsometer, X-Y stage and controller, wafer table vibration isolator for mounting stone surface plates to support the sample holder and the X-Y stage and the wafer transport equipment can be procured from one or more sources as set forth in the equipment table of FIG. 10.

When a microfabricated shape is provided such as when an electronic circuit is formed on the wafer 3, not only the coordinates of each measurement point $P_1$ to $P_n$ but also a recognition image for specifying the correct measurement point P may be recorded in the measurement point data Da.

Figure 3:
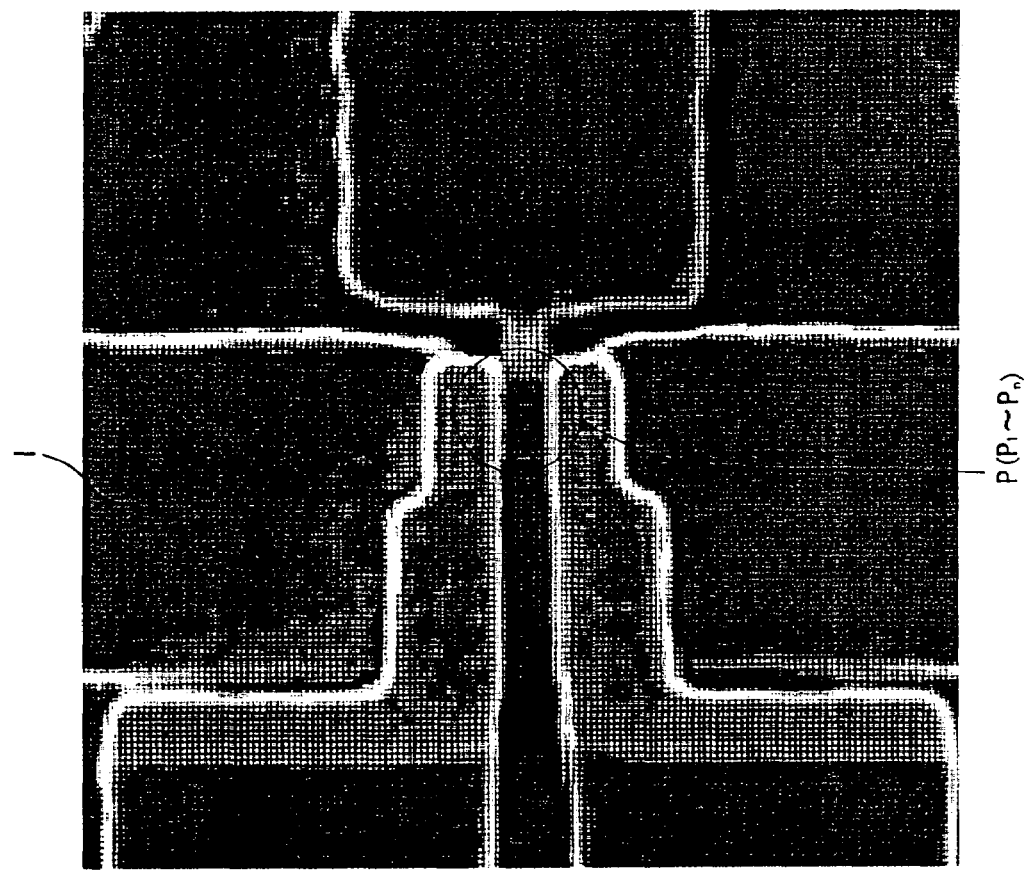
FIG. 3 is a view explaining one example of measurement points of the substrate inspection apparatus according to the first embodiment.

FIG. 3 is a view showing an example in which a specific position on the surface of the substrate can be provided with a microfabricated shape being defined as a measurement point. In FIG. 3, I is an image (recognition image) of the surface of the wafer 3 formed with a circuit pattern observed using the optical microscope 10, and the recognition image I is stored in the computer 60 as measurement point data Da for each measurement points $P_1$ to $P_n$.

The recognition image I is given for every measurement point $P_1$ to $P_n$ using the image when observing the surface of the first wafer 3 to set each measurement point $P_1$ to $P_n$. That is, when setting the measurement points $P_1$ to $P_n$, the surface of the wafer 3 is observed using the optical microscope 10, and the result is displayed on the screen and the like of the computer 60. The operator then operates the driving section 5 using the computer 60 to adjust the measurement points $P_1$ to $P_n$ while watching the screen. When the operator sets the measurement points $P_1$ to $P_n$, the computer 60 stores the coordinates of the measurement points $P_1$ to $P_n$ and the image picked up by the optical microscope 10 as the measurement point data Da.

When examining the second or the subsequent wafers 3 formed with the same circuit pattern, after placing the wafer 3 on the sample stage 4 by the conveying device 2B, sequentially selection of one measurement point P out of the coordinates of each measurement point $P_1$ to $P_n$ stored as the measurement point data Da, and controlling the driving section 5 in accordance with such coordinate is accomplished automatically by means of the computer 60. Fine adjustment of the measurement point P is performed by comparing the image observed using the optical microscope 10 with the recognition image I stored as the measurement point data Da and controlling the driving section 5 by such comparison.

As in the first embodiment, by recording the image observed by means of the optical microscope 10 at each measurement point $P_1$ to $P_n$ as the recognition image I, the control program Pa determines a predetermined part of the formed circuit pattern as the measurement point P in measurement and accurately measures the relationship between stress and film thickness of the relevant part even if the position of the wafer 3 on the sample stage 4 is shifted. That is, the generating condition of a partial stress caused by forming the circuit pattern and the film thickness and the like at the part where such stress is generated are measured in a comprehensive manner, and thus the examination of the wafer 3 is performed focusing on the part acting as the main part and the reliability of the examination is improved by such measures.

A unit pattern recognition system can include a CCD camera, video capture board, computer system and appropriate computer programs to process the video data. Components of such a system can be secured by a person of ordinary skill in this field from known sources such as set forth in the equipment table of FIG. 11.

Figure 4:
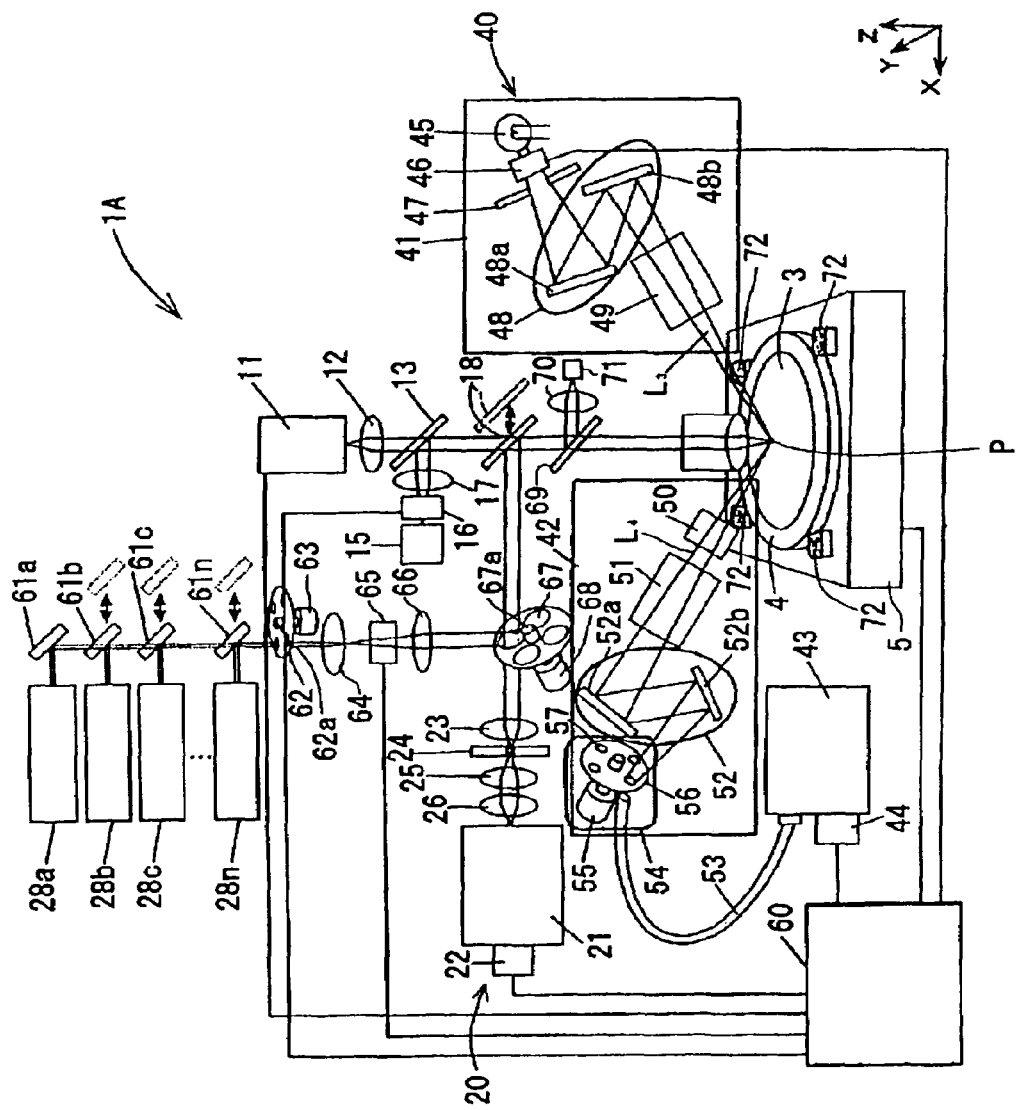
FIG. 4 is a view showing a configuration of a main part of a substrate inspection apparatus according to a second embodiment of the present invention.

FIG. 4 is a view showing a configuration of a main part of a substrate inspection apparatus 1A according to a second embodiment of the present invention. The substrate inspection apparatus 1A of the second embodiment includes a plurality of laser light sources 28a, 28b, 28c, 28n of different wavelength as the excitation light source for the Raman spectroscopic measurement in the Raman spectroscopy optical system 20. More specifically, the Ar lasers 28a, 28b, 28c, set to wavelengths of 514 nm, 488 nm, 310 nm, etc. and He—Cd ion laser 28n set to ultraviolet light of wavelength of 325 nm are used and a position movable light path switching mirrors 61a, 61b, 61c, 61n for selecting one of the laser light of different wavelength and leading the selected laser light to the wafer 3 to be measured are arranged at a position facing an oscillating part of the laser light sources 28a, 28b, 28c, 28n. By the way, for transmission of light from a laser source to Raman optical system, an optical fiber may be used.

Further, in addition to the collective lens 23 for adjusting the Raman light entering the spectroscope 21, the pin hole 24, the collimator lens 25, and the collective lens 26 for leading the collected light to the spectroscope 21, a laser light selecting device is arranged in the Raman spectroscopy optical system 20. This laser light selecting device includes a circular plate 62 attached with an optical filter (band pass filter) 62a for cutting the light of wavelength other than the excitation light exited from the laser light selected from a plurality of laser light sources 28a, 28b, 28c, 28n and rotated by a stepping motor 63, a collective lens 64, a laser light shutter 65 for shielding the laser light, a collimator lens 66 for changing the laser light to a collimated light, and a circular plate 67 attached with an optical filter 67a for leading the laser light to the wafer 3 and then cutting the Rayleigh light. The optical filter 67a is rotated by a stepping motor 68, and is capable of selectively and automatically switching the laser light for irradiating to the measurement point P of the wafer 3.

Further, in the Raman spectroscopic analysis, the ultraviolet light of wavelength of 325 nm can sometimes be used as the excitation light, and thus taking into consideration the fact that the focal points differ in an auto focus mechanism in which an image is obtained from the light entering the CCD camera 11 through the collective lens 12, a detector for detecting a focal point 71, for detecting the Rayleigh light intensity through the beam splitter 69 and the collective lens 70 arranged on the optical axis $L_1$, the same as the optical microscope 10 and movement controlling the driving section 5 of the sample stage 4 in the Z direction (vertical direction) is used so that the value of the detected Rayleigh light intensity is arranged to a maximum value to align the focal position.

Further, in the substrate inspection apparatus 1A according to the second embodiment, a data calibration sample 72 is arranged at a position in the vicinity of the sample stage 4 close to the wafer 3 to be measured. Desirably, for the data calibration sample 72, those in which the film thickness and the index of refraction are known in advance such as an NIST sample is used for the ellipsometer, and one or a plurality (four in the figure shown) of cut-outs formed by cutting the single crystal silicon without film or the strained silicon in which stress and composition are known in advance into a several dozen mm square is used for the Raman spectroscopy, but the number to be arranged or the type thereof may be selected arbitrarily.

Other configurations of the substrate inspection apparatus 1A according to the second embodiment are the same as those explained in the first embodiment, and thus the same reference characters are denoted for the relevant part or the relevant region, and a detailed explanation thereof is omitted.

According to the substrate inspection apparatus 1A of the second embodiment, advantages similar to the substrate inspection apparatus according of the first embodiment, in that both film thickness and index of refraction by the ellipsometer optical system 40 and stress and composition by the Raman spectroscopy optical system 20 at the same microscopic region are measured at high precision simultaneously output are achieved, plus it is possible to measure stress and composition with the Raman spectroscopy optical system 20, while distribution thereof in the depth direction is also easily measured.

Figure 5:
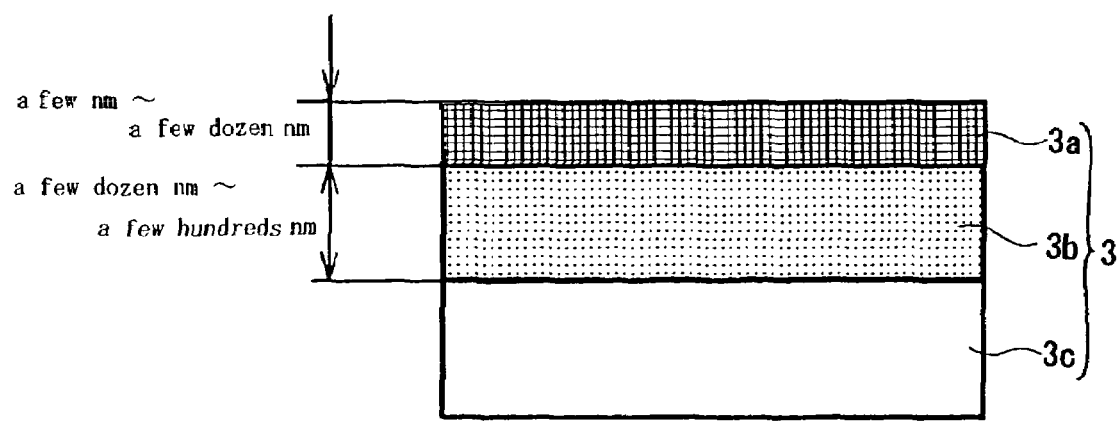
FIG. 5 is a cross sectional configuration view of a strained silicon substrate serving as one example of the substrate to be measured.

For instance, as shown in FIG. 5, when having the silicon wafer 3 formed with a few nm to a few dozen nm of strained silicon layer 3a, a few dozen nm to a few hundred nm of SiGe layer 3b, and a single crystal silicon substrate 3c stacked in such order from the surface as an object to be measured, the Raman spectrum resulting from the Si—Si band in the SiGe layer 3b may be detected at high intensity by selecting the Ar laser 28a of wavelength ($\lambda$=514 nm) having a large penetration depth of 760 nm and irradiating the laser light to the measurement point P, but at the same time, the Raman spectrum of the Si—Si band in the uppermost layer or the strained silicon layer 3a is influenced by the Raman spectrum of the Si—Si band of the single crystal silicon substrate 3c and thus it is difficult to detect, as shown in FIG. 6.

Only the Raman spectrum of the uppermost layer or the strained silicon layer 3a is measured by selecting the He—Cd ion laser 28n of wavelength ($\lambda$=325 nm) having a penetration depth of about 10 nm with the laser light selecting device and irradiating the ultraviolet light onto the measurement point P. In this case, when the laser light having an extremely small penetration depth is used, the excitation light does not reach the SiGe layer 3b and the Raman spectrum of the SiGe layer 3b may become impossible to detect, and thus although depending on the thickness of the uppermost layer 3a, the laser light having a wavelength that is barely influenced by the substrate 3c and that reaches the SiGe layer 3b must be selected.

Therefore, by selectively and automatically switching and irradiating laser light of different wavelengths in accordance with the stacked structure of the substrate to be measured or the thickness and the like of the uppermost layer or the strained silicon layer 3a, the distribution in the depth direction (film thickness direction) of stress or composition of the wafer 3 to be measured is easily and reliably detected without unduly being influenced by the substrate 3c. Thus even when a semiconductor substrate uses the strained silicon, mainly adopted in manufacturing recent semiconductor substrates, is to be measured, various physical quantities of internal stress of the strained silicon layer 3a, and further, composition and the like of the SiGe layer 3b acting as the base layer are reliably measured, and thus the substrate examination can be performed at a high precision.

Further, in a substrate inspection apparatus used in a semiconductor production line, repeatability in obtaining a stable measurement result over a long period of time is expected. Particularly, a high precision measurement of about 0.01/cm is required for stress measurement by means of the Raman spectral of silicon-based material, but in order to maintain the repeatability of such high precision measurement over a long period of time, temperature control of the sample (wafer) to be measured, variation control of the optical system involved in fluctuation of ambient environmental temperature, maintenance of performance of the optical filter and the like must be sufficiently considered.

In order to handle optical system fluctuations resulting from changes in ambient temperature, for example, wavelength deviation caused by slight distortion of optical parts, or positional shift of Raman spectral peak associated with temperature changes of semiconductor material itself to be measured, it is possible to take in gas laser plasma line together with Raman light (scattering light associated with irradiation of excitation light), correct the peak position of Raman spectra using the peak positional shift of this plasma line, and measure the stress from the peak position of the corrected Raman spectra. In such event, the atomic beam of emission lamp may be used in place of gas laser plasma line as a reference light (for wavelength calibration).

Figure 7:
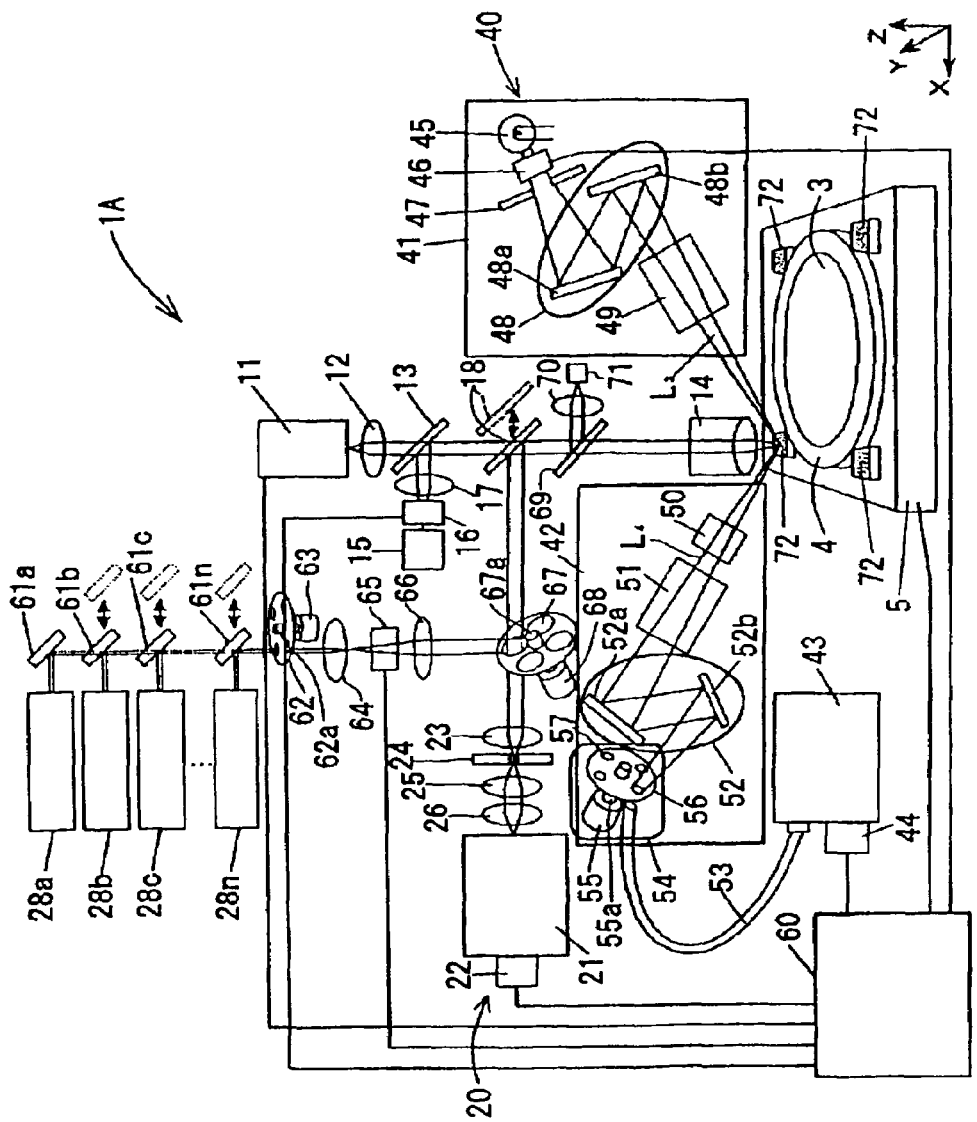
FIG. 7 is a configuration view of a main part showing a measurement state of a reference sample by the substrate inspection apparatus according to the second embodiment.

In the second embodiment, the driving section 5 is moved in the horizontal direction (X, Y directions) and the height direction (Z direction) so that a data calibration sample 72 arranged at a position in the vicinity of the sample stage 4 becomes the measurement point P, as shown in FIG. 7, at an arbitrary timing of for example, before or after a predetermined measurement of the wafer 3 to be measured, or in the middle of conveying the wafer 3 to the sample stage 4 by means of the robot arm 6.

By measuring film thickness and/or index of refraction of the data calibration sample 72 using the ellipsometer optical system 40 and measuring stress and/or composition of the data calibration sample 72 by using the Raman spectroscopy optical system 20, and calibrating the measurement values of the wafer 3 to be measured with the above measurement values as the reference, high precision can be maintained. Even if a wavelength shift is caused by a variation of the optical system such as deterioration of an optical filter or strain of the optical component resulting from fluctuation in the ambient environmental temperature, and further, if a shift in peak shift of the Raman spectrum is caused by a temperature influence of the wafer 3 to be measured, various physical quantities such as stress or composition, and film thickness or index of refraction are accurately measured irrespective of the fluctuation of the ambient environmental temperature, and thus the substrate examining precision may be maintained with satisfactory repeatability.

Figure 9:
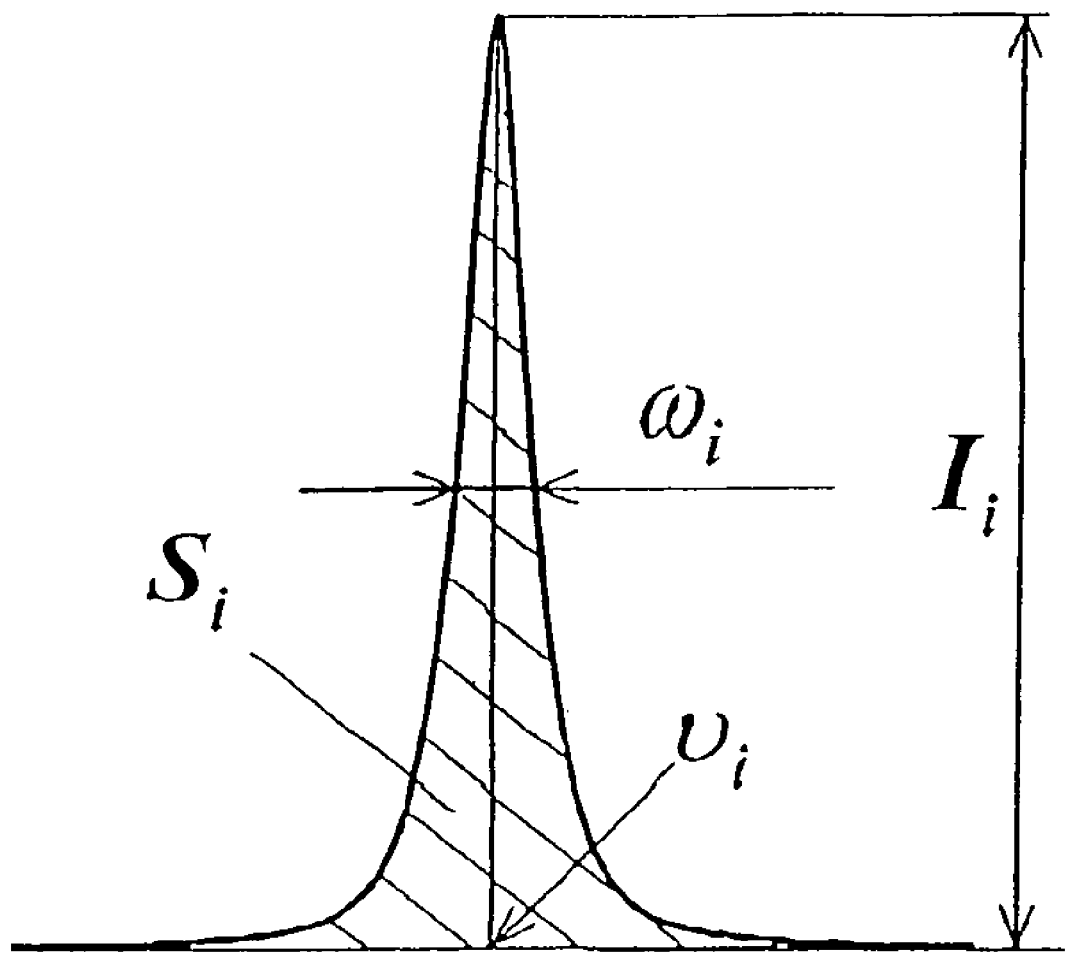
FIG. 9 is a representation of spectral parameters for a curve fitting calibration.

Specific examples for correcting sample spectra on the basis of spectra of data calibration sample 72 are described as follows:

Measurement Sequence
Calibration sample: Single crystal silicon
Reference light for wave number calibration: Gas laser plasma line
Measurement sequence 1 (measurement of calibrating samples, with correction)
1. Load wafer to stage (including alignment).
2. Move wafer to calibration sample measuring point.
3. Measure spectrum of calibration sample.
4. Compute spectral parameters of calibration sample (curve fitting treatment) see FIG. 9 for representative parameters.
[1] $\upsilon_{RO}, I_{RO}, \omega_{RO}, S_{RO}$
Plasma line spectral parameter for wave number calibration)
[2] $\upsilon_{R1}, I_{R1}, \omega_{R1}, S_{R1}$
(Spectral parameter of calibration sample)
[3] $\upsilon_{R1}' = (\rho_{R1} - \upsilon_{R0}) + C1$
[C1: correction value]
5. Move sample to the sample measurement point.
6. Measure sample spectrum.
7. Compute spectral parameters of sample.
[1] $\upsilon_{SO}, I_{SO}, \omega_{SO}, S_{SO}$
(Plasma line spectral parameter for wave number calibration)
[2] $\upsilon_{S1}, I_{S1}, \omega_{S1}, S_{S1}$
(Sample spectral parameter 1)
[3] $\upsilon_{S2}, I_{S2}, \omega_{S2}, S_{S2}$
Sample spectral parameter 2)
[4] Correction of peak shift $$\upsilon_{S1}' = (\upsilon_{S1} - \upsilon_{SO}) + C1$$

$$\upsilon_{S2}' = (\upsilon_{S2} - \upsilon_{SO}) + C1$$

[c1: correction value]
8. Correct sample spectrum parameters.
[1] Peak shift $$\upsilon_{S1}'' = (\upsilon_{S1}' - \upsilon_{R1}') + C2$$

$$\upsilon_{S2}'' = (\upsilon_{S2}' - \upsilon_{R1}') + C2$$

[c2: correction value: in the case of single crystal silicon: 520.7 cm$^{-1}$]
[2] Peak intensity $$I_{s1}' = I_{s1}/I_{R1}$$

$$I_{s2}' = I_{s2}/I_{R2}$$

[3] Half-value width $$\omega_{S1}' = (\omega_{S1} - \omega_{R1}) + C3$$

$$\omega_{S2}' = (\omega_{S2} - \omega_{R1}) + C3$$

[c3: correction value: dependent on spectrum measurement conditions]
[4] Band area $$S_{S1}' = S_{S1}/S_{R1}$$

$$S_{S2}' = S_{S2}/S_{R1}$$

9. Compute output (result display) parameters.
Ex. Computation of stress value $$\sigma_{S1} = A \times \Delta\upsilon_{S1}', \quad \Delta\upsilon_{S1}' = \upsilon_{S1}' - \upsilon_{R1}' \text{ (cm}^{-1}\text{)} \quad [1]$$

$$\sigma_{S2} = A \times \Delta\upsilon_{S2}', \quad \Delta\upsilon_{S2}' = \upsilon_{S2}' - \upsilon_{R1}' \text{ (cm}^{-1}\text{)} \quad [2]$$

[A (MPa/cm$^{-1}$): parameter set for every material and measurement condition]
10. Repeat Paragraphs 4 through 8 until measurements at all the established measurement points are finished.
11. Unload wafer.

Measurement Sequence 2 (Measurement of Calibration Samples, Without Correction)
1. Load wafer to stage (including alignment).
2. Move wafer to calibration sample measuring point.
3. Measure spectrum of calibration sample.
4. Compute spectral parameters of calibration sample (curve fitting treatment)
[1] $\upsilon_{SO}, I_{SO}, \omega_{SO}, S_{SO}$
(Plasma line spectral parameter for wave number calibration)
[2] $\upsilon_{S1}, I_{S1}, \omega_{S1}, S_{S2}$
(Sample spectral parameter 1)
[3] $\upsilon_{S2}, I_{S2}, \omega_{S2}, S_{S2}$
(Sample spectral parameter 2)
[4] Correction of peak shift $$\upsilon_{S1}' = (\upsilon_{S1} - \upsilon_{SO}) + C1$$

$$\upsilon_{S2}' = (\upsilon_{S2} - \upsilon_{SO}) + C1$$

[c1: correction value]

5. Compute output (result display) parameters.

Ex. Computation of stress value $$\sigma_{S1} = A \times \Delta\upsilon_{S1}', \Delta\upsilon_{S1}' = \upsilon_{S1}' - 520.7 \text{ (cm}^{-1}) \quad [1]$$

$$\sigma_{S2} = A \times \Delta\upsilon_{S2}', \Delta\upsilon_{S2}' = \upsilon_{S2}' - 520.7 \text{ (cm}^{-1}) \quad [2]$$

[A (MPa/cm$^{-1}$): parameter set for every material and measurement condition]

6. Repeat Paragraphs 4 through 8 until measurements at all the established measurements points are finished.

7. Unload wafer.

Figure 8:
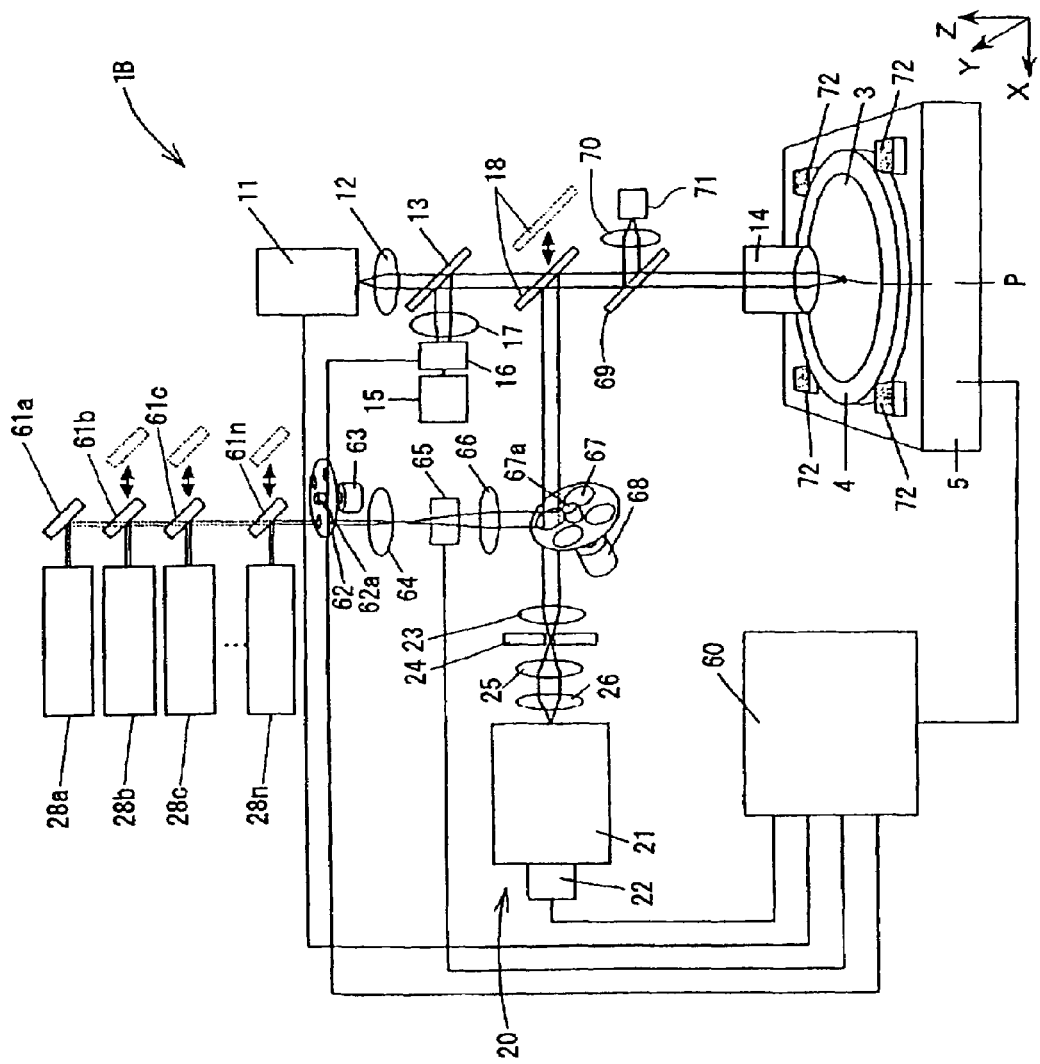
FIG. 8 is a view showing a configuration of a main part of a substrate inspection apparatus according to a third embodiment of the present invention.

FIG. 8 is a view showing a configuration of a main part of a substrate inspection apparatus 1B according to a third embodiment of the present invention. The substrate inspection apparatus 1B of the third embodiment is configured by omitting the ellipsometer optical system 40 in the substrate inspection apparatus 1 according to the first embodiment and the substrate inspection apparatus 1A according to the second embodiment explained above, and including the Raman spectroscopy optical system 20 and an arithmetic processing unit (computer) 60, which Raman spectroscopy optical system 20, similar to the second embodiment, includes a plurality of laser light sources 28a, 28b, 28c, 28n of different wavelength as the excitation light source for Raman spectroscopic measurement. This embodiment includes a data calibration sample 72 at a position in the vicinity of the sample stage 4 close to the wafer 3 to be measured. Here, other configurations of the Raman spectroscopy optical system 20 are the same as the configurations of the second embodiment and thus the same reference characters are denoted for the relevant part and the relevant region, and a detailed explanation thereof is omitted.

According to the substrate inspection apparatus 1B of the third embodiment, by selectively and automatically switching and irradiating the laser light of different wavelength from a plurality of laser light sources 28a, 28b, 28c, 28n to the wafer 3 in accordance with the stacked structure of the wafer 3 to be measured and the thickness and the like of the uppermost layer, the distribution in the depth direction (film thickness direction) of stress or composition of the wafer 3 to be measured can be easily and reliably detected without undue influence by the substrate. Thus even having a semiconductor substrate using the strained silicon, as the object to be measured, not only are various physical quantities such as internal stress of the strained silicon and composition of the SiGe layer acting as the base layer reliably measured and the substrate examination is performed at high precision, but further, stress and/or composition of the data calibration sample 72 is measured as necessary using the Raman spectroscopy optical system 20, and the measurement values of the wafer 3 to be measured are calibrated with the above measurement values as the reference. Stress or composition of the wafer 3 to be measured can be accurately measured irrespective of fluctuation in the ambient environmental temperature, thereby improving the substrate examination precision and achieving a long term repeatability.

When using a single crystal silicon as the data calibration sample 72, the relationship between the temperature and the peak shift of the single crystal Raman spectrum and the relationship between the temperature of the data calibration sample 72 and the temperature of the sample (wafer) 3 to be measured are accurately measured in advance. Further, with a spectrum half bandwidth and the spectrum peak intensity obtained by measuring the data calibration sample 72 using the Raman spectroscopy optical system 20 at a normal state as the reference, normality/abnormality of the Raman spectroscopy optical system 20 is determined by comparing the spectrum half bandwidth and the spectrum peak intensity obtained when measuring the data calibration sample 72 with the reference values as necessary. Particularly, a variation of intensity is often caused by deterioration of the optical filter, shift of an optical axis, or variation of output power from the laser light source and the like, and thus the abnormal part in the substrate inspection apparatus is easily identified by monitoring the intensity value.

In addition, a thermometer may be attached to the data calibration sample 72 itself to allow direct measurement of the temperature change of the data calibration sample 72. In this case, the fluctuation of the ambient environmental temperature is immediately detected and is effectively used in calibrating the measurement values of the wafer 3 to be measured. The ellipsometer may be either a spectroscopic ellipsometer or a single wavelength ellipsometer.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:

1. A substrate inspection apparatus comprising:
   a sample stage configured to be movable;
   a conveying device for conveying a sample to be measured to the sample stage;
   an optical microscope for observing a measurement point on the sample to be measured on the sample stage;
   an ellipsometer optical system for irradiating polarized light of multiple wavelengths to the measurement point and outputting information relating to the sample to be measured;
   a Raman spectroscopy optical system for irradiating a laser light to the measurement point of the optical microscope and outputting information relating to the sample to be measured; and
   an arithmetic processing unit for analyzing and outputting stress and/or composition in addition to film thickness and/or index of refraction at the measurement point using the obtained information.

2. The substrate inspection apparatus as claimed in claim 1 wherein:
   a plurality of laser light sources of different wavelength and a laser light selecting device for selectively and automatically switching the laser light for irradiating to the measurement point on the sample to be measured from the plurality of laser light sources are arranged in the Raman spectroscopy optical system.

3. The substrate inspection apparatus as claimed in claim 1, further comprising a calibration sample arranged at a position in the vicinity of the sample to be measured, whereby information relating to the sample output from the ellipsometer optical system and the Raman spectroscopy optical system can be desirably calibrated by a comparison measurement of the calibration sample as necessary with the ellipsometer optical system and the Raman spectroscopy optical system.

4. The substrate inspection apparatus as claimed in claim 1, further comprising a device for measurement by means of the ellipsometer optical system and the Raman spectroscopy optical system after performing a position adjustment in the height direction of the sample stage while checking the position of the focal point thereof by using one of an image observed by the optical microscope and the intensity of the light obtained when the laser light is irradiated to the sample.

5. The substrate inspection apparatus as claimed in claim 1, wherein the arithmetic processing unit includes examination recipe data including coordinates indicating the position of the measurement point on the sample, measurement condition containing information of wavelength region of the light used in the Raman spectroscopy optical system and the ellipsometer optical system, the accumulated time in detection, and the analytical curve used, an examination result output condition indicating the output pattern of the examination result, and further includes an automatic examination function for sequentially performing the same examination on a plurality of samples to be measured in accordance with the examination recipe data.

6. The substrate inspection apparatus as claimed in claim 5, further comprising that the arithmetic processing unit stores a recognition image formed by an image observed by the optical microscope at the measurement point on the sample to be measured as the data indicating the position of the measurement point of the examination recipe data, and measurements using the ellipsometer optical system and the Raman spectroscopy optical system is performed after moving the sample stage in the direction of the plane surface and adjusting the plane surface position of the measurement point by comparing the image obtained by observing the surface of the sample to be measured with the optical microscope and the recognition image.

7. A substrate inspection apparatus comprising:
a sample stage configured so as to be movable;
a conveying device for conveying a sample to be measured to the sample stage;
an optical microscope for observing a measurement point on the sample to be measured on the sample stage;
a Raman spectroscopy optical system for irradiating a laser light to the measurement point of the optical microscope and outputting information relating to the sample to be measured; and
an arithmetic processing unit for analyzing and outputting stress and/or strain at the measurement point using the obtained information,
wherein a plurality of laser light sources of different wavelength and a laser light selecting device capable of selectively and automatically switching the laser light for irradiating to the measurement point on the sample from the plurality of laser light sources are arranged in the Raman spectroscopy optical system.

8. A substrate inspection apparatus comprising:
a sample stage configured so as to be movable;
a conveying device for conveying a sample to be measured to the sample stage;
an optical microscope for observing a measurement point on the sample to be measured on the sample stage;
a Raman spectroscopy optical system for irradiating a laser light to the measurement point of the optical microscope and outputting information relating to the sample to be measured;
an arithmetic processing unit for analyzing and outputting stress and/or strain at the measurement point using the obtained information; and
means for arranging a calibration sample at a position in the vicinity of the sample to be measured on the sample stage, and the information relating to the sample to be measured which is output from the Raman spectroscopy optical system can be desirably calibrated with the information obtained by measuring the calibration sample by means of the Raman spectroscopy optical system as the reference.

9. A method of examining a semiconductor substrate, comprising:
a semiconductor substrate for examination;
determining a measurement point as an initial position for examination;
irradiating polarized light of a plurality of different wavelengths to the measurement point and detecting first output signals from the polarized light by an ellipsometer measurement system;
irradiating laser light of a predetermined wavelength to the measurement point and detecting second output signals from the laser light by a Raman spectroscopy measurement system; and
processing the first output signals and the second output signals to determine the suitability of the semiconductor substrate and providing an output signal representative of the examination of the semiconductor substrate.

10. The method of claim 9 wherein the processing is based on sequential first output signals and second output signals taken substantially at the same time and measurement point.

11. The method of claim 10 wherein the processing determines a plurality of conditions from stress, composition, film thickness and index of refraction in determining suitability of the semiconductor substrate.

12. The method of claim 11 wherein a plurality of measurement points with corresponding first output signals and second output signals are automatically examined on the semiconductor substrate.

13. The method of claim 12 wherein a plurality of different laser lights of different predetermined wavelengths are used to provide second output signals.

14. The method of claim 13 wherein the position of the semiconductor substrate relative to the laser light sources are adjusted to compensate for the predetermined wavelengths.

15. The method of claim 14 further including providing a calibration sample and calibrating the substrate examining device automatically before detecting the first and second output signals.

16. A substrate inspection apparatus comprising:
a sample stage configured so as to be movable;
a piezo drive unit for moving the sample stage;
a conveying device for conveying a sample to be measured to the sample stage;
an optical microscope for observing a measurement point on the sample to be measured on the sample stage;
a Raman spectroscopy optical system for irradiating a laser light to the measurement point of the optical microscope and outputting information relating to the sample to be measured;
an arithmetic processing unit for analyzing and outputting stress and/or strain at the measurement point using the obtained information; and
a driving unit for adjusting a height direction of the sample stage while checking the position of the focal point thereof by using one of an image observed by the optical microscope and the intensity of the light obtained when the laser light is irradiated to the sample.

17. A substrate inspection apparatus comprising:
a sample stage configured so as to be movable;
a conveying device for conveying a sample to be measured to the sample stage;
an optical microscope for observing a measurement point on the sample to be measured on the sample stage;

a Raman spectroscopy optical system for irradiating a laser light to the measurement point of the optical microscope and outputting information relating to the sample to be measured; and an arithmetic processing unit for analyzing and outputting stress and/or strain at the measurement point using the obtained information, wherein the arithmetic processing unit includes examination recipe data including coordinates indicating the position of the measurement point on the sample, measurement condition containing information of wavelength region of the light used in the Raman spectroscopy optical system, the accumulated time in detection, and the analytical curve used, and an examination result output condition indicating the output pattern of the examination result, and further including an automatic examination function for sequentially performing the same examination on a plurality of samples to be measured in accordance with the examination recipe data.

18. The substrate inspection apparatus as claimed in claim 17, further comprising that the arithmetic processing unit stores a recognition image formed by an image observed by the optical microscope at the measurement point on the sample to be measured as the data indicating the position of the measurement point of the examination recipe data, and measurements using the Raman spectroscopy optical system is performed after moving the sample stage in the direction of the plane surface and adjusting the plane surface position of the measurement point by comparing the image obtained by observing the surface of the sample to be measured with the optical microscope and the recognition image.

19. The substrate inspection apparatus of claim 1, wherein the sample stage is configured to be movable via a piezo drive.

20. The substrate inspection apparatus of claim 7, wherein the sample stage is configured to be movable via a piezo drive.

21. The substrate inspection apparatus of claim 8, wherein the sample stage is configured to be movable via a piezo drive.

22. The substrate inspection apparatus of claim 17, wherein the sample stage is configured to be movable via a piezo drive.

* * * * *